United States Patent
Kuida et al.

(10) Patent No.: US 7,323,616 B2
(45) Date of Patent: Jan. 29, 2008

(54) GENETICALLY ALTERED MICE DEFICIENT IN FUNCTIONAL CASPASE-9

(75) Inventors: Keisuke Kuida, Lexington, MA (US); Richard A. Flavell, Guilford, CT (US)

(73) Assignees: Vertex Pharmaceuticals, Inc., Cambridge, MA (US); Yale University, New Haven, CT (US)

( * ) Notice: Subject to any disclaimer, the term of this patent is extended or adjusted under 35 U.S.C. 154(b) by 0 days.

(21) Appl. No.: 09/728,173

(22) Filed: Dec. 1, 2000

(65) Prior Publication Data

US 2004/0255343 A1 Dec. 16, 2004

Related U.S. Application Data

(63) Continuation of application No. PCT/US99/11861, filed on May 28, 1999.

(60) Provisional application No. 60/087,711, filed on Jun. 2, 1998.

(51) Int. Cl.
- A01K 67/027 (2006.01)
- A01K 67/063 (2006.01)
- G01N 33/00 (2006.01)
- C12N 15/00 (2006.01)

(52) U.S. Cl. .................... 800/18; 800/3; 800/9; 800/25

(58) Field of Classification Search .................. 800/21, 800/8, 18, 25, 3, 9
See application file for complete search history.

(56) References Cited

U.S. PATENT DOCUMENTS

| | | | |
|---|---|---|---|
| 6,010,878 | A | 1/2000 | Dixit et al. |
| 6,218,511 | B1 | 4/2001 | Goldmakher et al. |
| 6,294,169 | B1 | 9/2001 | Dixit et al. |
| 6,605,426 | B1 | 8/2003 | Goldmakher et al. |
| 6,890,721 | B1 | 5/2005 | Dixit et al. |
| 2003/0105046 | A1 | 6/2003 | Yuan et al. |
| 2003/0198949 | A1 | 10/2003 | Goldmakher et al. |
| 2003/0207262 | A1 | 11/2003 | Goldmakher et al. |
| 2005/0089984 | A1 | 4/2005 | Dixit et al. |

FOREIGN PATENT DOCUMENTS

| | | |
|---|---|---|
| EP | 0808904 | 11/1997 |
| EP | 0842665 | 5/1998 |
| WO | WO96/12025 | 4/1996 |
| WO | WO-97/46663 | 12/1997 |
| WO | WO98/06263 | 2/1998 |
| WO | WO-98/57664 | 12/1998 |
| WO | WO-99/60171 | 11/1999 |

OTHER PUBLICATIONS

Strunk et al. (2004) Phenotypic variation resulting from a deficiency of epidermal growth factor receptor in mice is caused by extensive genetic heterogeneity that can be genetically and molecularly partitioned. Gentics 167:1821-1832.*
Leneuve et al. (2003) Cre-mediated germline mosaicism:a new transgenic mouse for the selective removal of residual markers from tri-lox conditional alleles. Nucleic Acids Research. 31:1-8.*
Sanford et al. (2001) Influence of Genetic Background on knockout mouse phenotypes. Methods Mol. Biol. 158:217-225.*
Cameron et al. (1997) Recent Advances in Transgenic Technology. Molecular Biotechnology. 7:253-265.*
Wall et al. (1996) Transgenic Livestock: Progress and prospects for the future. Theriogenology 45:57-68.*
Houdebine et al. (1994) Production of pharmaceutical proteins from transgenic animals. Journal of Biotechnology. 34:269-287.*
Villa et al., "Capases and caspase inhibitors," TIBS Trends in Biochemical Sciences, 22(10):388-393, (1997).
Duan H. et al., "ICE-LAP6 a novel member of the ICE/Ced-3 gene family."; J. Bio. Chem; vol. 6, No. 28; Jul. 12, 1996 pp. 16720-16724.
Hakem R. etlal., "Differential requirement for caspase 9.." CELL; Vo. 94, No. 3; Aug. 7, 1998; pp. 339-352.
Kuida K. et al., "Reduced apoptosis and cytochrom c-mediated caspase.."; CELL, vol. 9, No. 3, Aug. 7, 1998; pp. 325-337.
Kuida K. eteal., "Decreased apoptosis in the brain and.." NATURE, vol. 384, No. 6607; Nov. 28, 1996; pp. 368-372.
Li Peng, et al., "Cytochrom c and dATP-dependent formation of.."; CELL, Vo. 91, No. 4.; Nov. 14, 1997; pp. 479-489.
Soengas M.,et al. ; "Apaf-1 and caspase-9 in p53 dependent . . . "; SCIENCE, Vo. 284, No. 5411; Feb. 4, 1999, pp. 156-159.

* cited by examiner

*Primary Examiner*—Deborah Crouch
(74) *Attorney, Agent, or Firm*—Ropes & Gray LLP

(57) ABSTRACT

The invention relates to genetically manipulated animals that are deficient in the expression of Caspase-9, a protein involved in programmed cell death. The invention further relates to methods for preventing specific types of cell death associated with Caspase-9 activation.

10 Claims, 11 Drawing Sheets

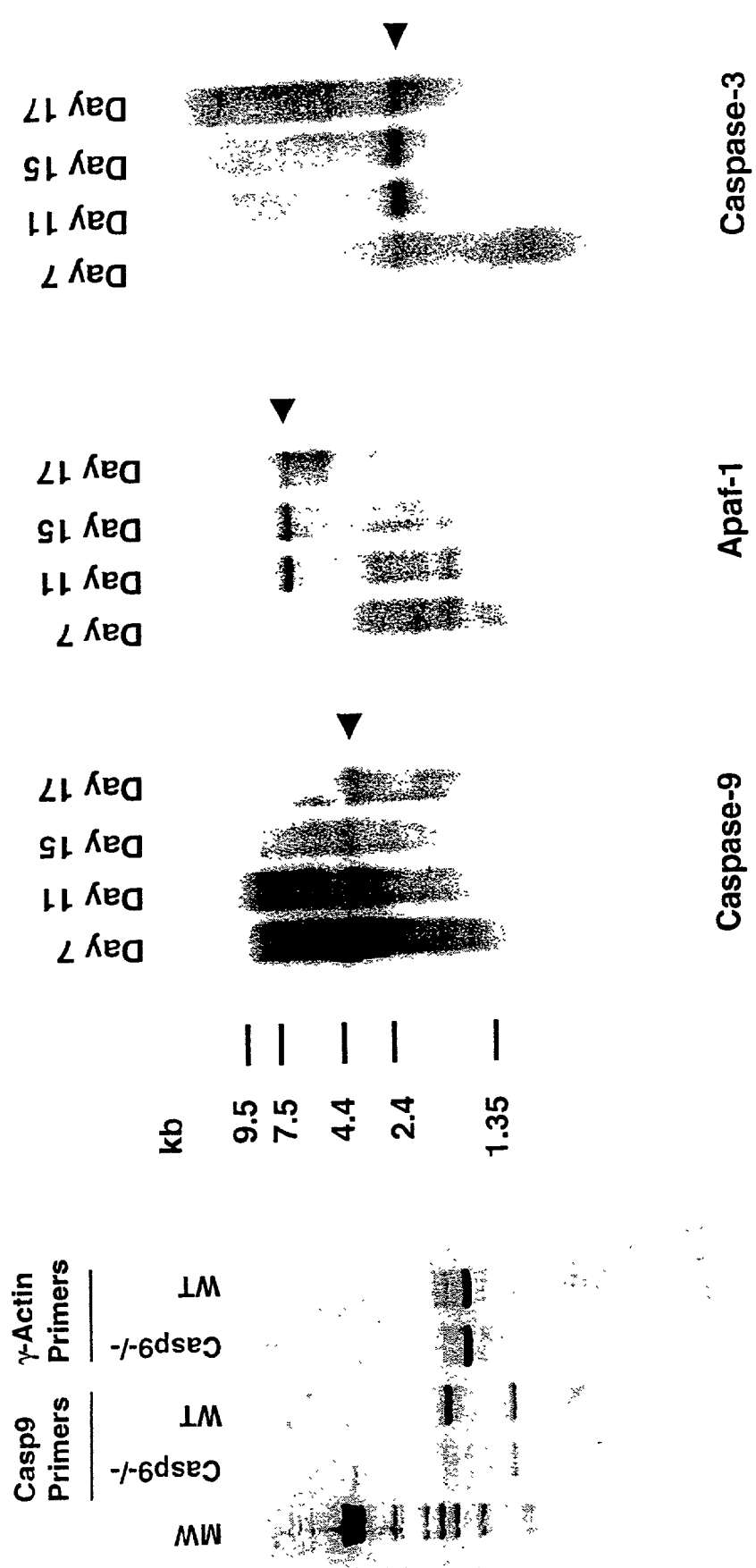

```
                         SEQUENCE LISTING

<160> NUMBER OF SEQ ID NOS:  7

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 1
atggacgaag cggatcggcg gc                                             22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
ttatgatgtt ttaaagaaaa g                                              21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
gccatggacg aagcggatcg gcgg                                           24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
ggcctggatg aagaagagct tggg                                           24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer
```

```
<400> SEQUENCE: 5
gggaagatgg atgcaaaagc tcga                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
atggctgcaa ttcttctctg taag                                              24

<210> SEQ ID NO 7
<211> LENGTH: 5
<212> TYPE: PRT
<213> ORGANISM: mammalian
<220> FEATURE:
<221> NAME/KEY: UNSURE
<222> LOCATION: (4)
<223> OTHER INFORMATION: X is arginine or glycine
<221> NAME/KEY: DOMAIN
<222> LOCATION: (1)..(5)
<223> OTHER INFORMATION: Pentapeptide motif common to all known caspases

<400> SEQUENCE: 7

Gln Ala Cys Xaa Gly
 1               5
```

+/-

-/-

+/-

-/-

+/-

-/-

GENETICALLY ALTERED MICE DEFICIENT IN FUNCTIONAL CASPASE-9

CROSS-REFERENCE TO RELATED APPLICATIONS

This application is a continuing application of co-pending International Patent Application PCT/US99/11861, filed May 28, 1999, which claims priority of United States provisional patent application 60/087,711, filed Jun. 2, 1998.

TECHNICAL FIELD OF THE INVENTION

The invention relates to genetically manipulated animals that are deficient in the expression of Casaspe-9, a protein involved in programmed cell death. The invention further relates to methods for preventing specific types of cell death associated with Caspase-9 activation.

BACKGROUND OF THE INVENTION

Apoptosis is an important biological function for maintaining homeostasis in multicellular organisms. This process is genetically determined and has been shown as one of basic mechanisms conserved during evolution [M. D. Jacobsen et al., Cell, 88, pp. 347-54 (1997)].

The process of cell death in mammals involves members of the Caspase gene family, which consists of at least ten members [E. S. Alnemri et al., Cell, 87, p. 171 (1996)]. All caspases are cysteine proteases and synthesized as a precursor form. Caspases are activated by cleavage of the precursor at specific Asp residues. This generates an active heterodimer consisting of a 20 kDa and a 10 kDa subunit. This heterodimer then dimerizes with itself forming a tetramer. Activation of caspases is probably mediated by autocatalytic processes or a cascade among the caspase proteases. Once caspases are activated, they cleave a variety of target proteins causing changes in cells associated with apoptosis.

Recent work on the apoptotic process has revealed that activation of Caspase-3 is associated with DNA fragmentation [X. Liu et al., Cell, 89, pp. 175-84 (1997)]. Three factors are involved in Caspase-3 activation—Apaf-1 (apoptosis protease activating factors), cytochrome-c (which is a essential element for mitochondrial functions) and Caspase-9 [Zou et al. (1997); X. Liu et al. (1996), Cell, 86, pp. 147-57; and P. Li et al., Cell 91 pp. 479-89 (1997)].

Understanding the mechanisms of programmed cell death has important implications for preventing developmental abnormalities, as well as in the prevention of nerve cell death, smooth and cardiac muscles degeneration, and cell death associated with viral infection. Thus, there is a great need to obtain tools to study apoptosis, as well as developing inhibitors thereof.

SUMMARY OF THE INVENTION

The present invention provides methods for producing animals, particularly mice, deficient in Caspase-9 expression. The invention also relates to genetically altered animals which do not express functional Caspase-9. Such animals may be produced by the methods of this invention or by related methods.

The Caspase-9 deficient animals of this invention show abnormality in the brain. Supernumerary cells are found in the forebrain, the hindbrain and the spinal cord. Moreover, apoptosis and DNA fragmentation are reduced in dexamethasone-treated thymocytes obtained from the Caspase-9 deficient animals of this invention. These and other data presented herein demonstrate that Caspase-9 is an upstream caspase responsible for the activation of one or more other caspases in the caspase cascade. Thus, Caspase-9 plays an important in neuronal apoptosis, cardiac and smooth muscle apoptosis and apoptosis associated with viral infection.

Thus, another aspect of the present invention relates to method for preventing apoptosis by inhibiting Caspase-9 activity. Such inhibitors include polyclonal and monoclonal antibodies specific for Caspase-9, anti-sense nucleotides which specifically hybridize to Caspase-9 DNA or mRNA, tailor-made enzymatic nucleotides akin to ribozymes that specifically cleave Caspase-9 mRNA, and other molecules discussed below.

DETAILED DESCRIPTION OF THE INVENTION

Figure 1A:
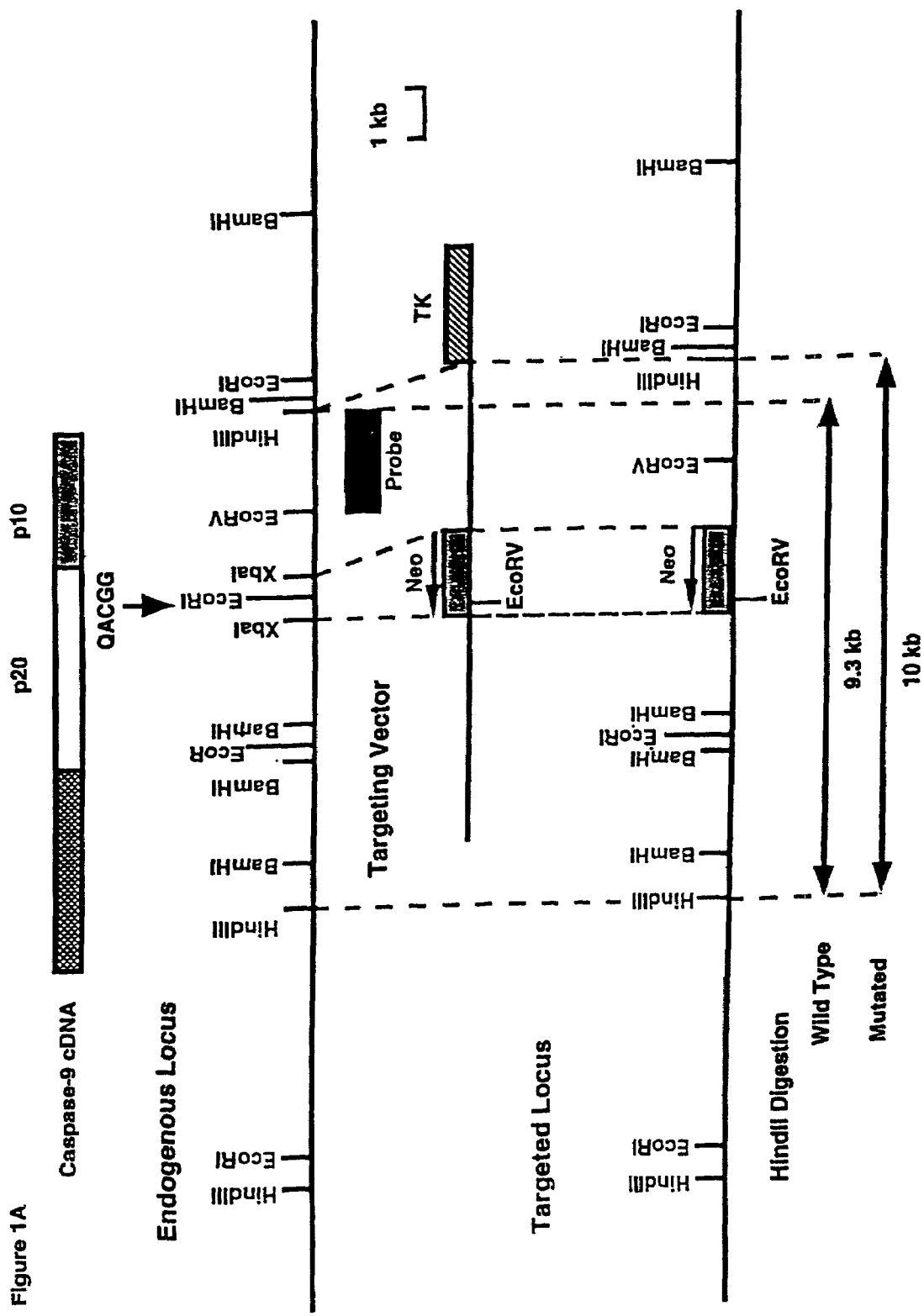
FIG. 1, panel A, depicts the cloning strategy for creating a non-functional Caspase-9 gene. Panel B depicts the electrophoresis of reverse transcribed-PCR amplified mRNA from a Caspase-9 knockout mouse and a wild-type mouse primed with a Caspase-9 specific primer or with an actin-specific primer. Panel C depicts a Northern blot of total mRNA from different aged wild-type mouse embryos probed with caspase-9-, caspase-3- and apaf-1-specific probes.

The present invention provides genetically altered animals that are defective in Caspase-9 expression. The term "animals", as used herein include all mammals, except human beings. Preferably, the genetically altered animal is a rodent. More preferably, it is a mouse.

The first step in the creation of the genetically altered animals of this invention is the provision of a Caspase-9 genomic clone. This may be achieved by probing a genomic library with a Caspase-9 specific probe. Such probes can be Caspase-9-specific primers that, when utilized in conjunction with PCR technology, amplify Caspase-9 specific genomic DNA. Alternatively, the probe may be a caspase-9 cDNA or fragment thereof. Such a cDNA may also be obtained by probing a cDNA library with Caspase-9-specific primers, followed by PCR. Alternatively, the cDNA may be made by specifically reverse transcribing mRNA encoding Caspase-9 through the use of Caspase-9 specific primers. Caspase-9 specific primers are set forth in the examples below.

Once the genomic clone is isolated, the DNA must be mutated so as to render it incapable of encoding a functional Caspase-9 protein. This may be achieved by a variety of methods well known in the art, such as site-directed mutagenesis or excision of part of the coding region of the gene, with or without concomitant replacement of the excised DNA with alternate DNA.

It is known that the pentapeptide motif QACXG (where "X" is arginine or glycine; SEQ ID NO:7) is conserved among members of the Caspase family and appears to be necessary for activity. Accordingly, deletion or mutation of the DNA encoding this portion of Caspase-9 is will render the resulting gene unable to express a functional Caspase-9. It is preferred that the DNA encoding this portion of Caspase-9 be replaced with DNA encoding a marker gene so that cells transformed with the resulting DNA can be easily identified. Preferably, the region of the genomic clone containing the pentapeptide motif is replaced by DNA encoding the neo gene, which can later serve as a marker for transformants.

The ultimate construct containing the non-functional Caspase-9 gene is then linearized and introduced to or transfected into used to transform a cell type that is from the same species as the desired genetically altered animal. Preferably, that cell type is an embryonic stem cell. The ultimate goal is to have homologous recombination occur between the wild-type Caspase-9 gene in the chromosomes of the cell and the mutant Caspase-9 gene in the vector. Cells containing this mutated Caspase-9 gene are identified via the marker gene.

In the case of the neo marker gene, we looked for cells that were resistant to G418 and gancyclovir. Homologous recombination is confirmed by Southern blotting using a probe specific for the marker gene.

Once a recombinant cell has been identified, it is then injected into a balstocyst from the desired species. The resulting chimeric animal is then bred to a normal animal to produce heterozygous offspring. These offspring are then interbred to obtain an animal homozygous for a non-functional Caspase-9 gene.

Confirmation of having produced a genetically altered animal defective in Caspase-9 production can be achieved by analysis of that animal's mRNA or expressed proteins, for the absence of molecules corresponding to Caspase-9 (mRNA or protein).

According to another embodiment, the invention provides a method of treating or preventing a disease or condition associated with Caspase-9 expression. In particular, the invention provides a method of treating or preventing developmental abnormalities, nerve cell death, smooth and cardiac muscle degeneration and cell death associated with viral infection.

The method of this invention comprises the step of administering to a patient suffering from said disease or condition a pharmaceutically acceptable composition comprising a molecule which inhibits either the expression of Caspase-9 or the activity of Caspase-9. Such molecules include, but are not limited to, monoclonal and polyclonal antibodies specific for Caspase-9 or epitopes thereof, oligonucleotides that specifically hybridize to Caspase-9 DNA so as to prevent transcription of functional Caspase-9 mRNA, oligonucleotides that specifically hybridize to Caspase-9 mRNA to as to prevent expression of Caspase-9 and ribozymes that specifically cleave Caspase-9 mRNA.

Given that both the genomic DNA sequence, the cDNA sequence and the amino acid sequence of Caspase-9 is known, the creation of the various Caspase-9 inhibitors referred to above (at the DNA, mRNA and protein level) is well within the ordinary skill of the art.

In order that this invention be more fully understood, the following examples are set forth. These examples are for the purpose of illustration only and are not to be construed as limiting the scope of the invention in any way.

EXAMPLE 1

Generation of Caspase-9 Deficient Mice

Human caspase-9 cDNA was amplified by PCR from Jurkat cells using caspase-9 -specific primers (5'-ATG GAC GAA GCG GAT CGG CGG C-3' (SEQ ID NO:1) and 5'-TTA TGA TGT TTT AAA GAA AAG-3' (SEQ ID NO:2)). 129SV/J genomic library (Stratagene) was screened with the cDNA to obtain a mouse caspase-9 genomic clone. An eight kb HindIII-NotI fragment containing a portion encoding the pentapeptide motif conserved among Caspase family members was subcloned into pBlueScript (Stratagene). The resulting plasmid was digested with XbaI and blunted. An EcoRI-HindIII fragment of the neo gene cassette [K. Nakayama et al., *Science*, 261, pp. 1584-88 (1993)] was also blunted and ligated to the plasmid containing the mouse caspase-9 genomic fragment. The plasmid was then digested with XhoI and NotI and subcloned into the tk cassette vector [K. Nakayama et al. (1993), supra]. The resulting vector, shown in FIG. 1A includes a neo gene cassette, which replaces a 1.0 kb XbaI fragment encoding the active pentapeptide motif (QACGG), flanked by 7 kb of caspase-9 genomic sequence.

The construct was linearized by NotI and transfected into W9.5 ES cells. Clones resistant to G418 and gancyclovir were selected and homologous recombination was confirmed by Southern blotting. One out of 32 clones screened was positive for homologous recombination and single integration of the construct was verified by hybridization with the neo-specific probe.

Chimeric mice were generated by injection of this clone into C57BL/6 blastocysts. The resulting male chimera mice were bred to C57BL/6 females to obtain heterozygous mice.

Inter-breeding of the heterozygous mice was performed to generate Caspase-9 deficient mice. Inter-breeding of heterozygous mice generated postnatal Caspase-9 −/− mice at a frequency less than 2% of the total number of mice screened, while the knockout embryos were collected at a Mendelian ratio up to the age of embryonic day (E)16.5 (see Table 1, below). Most of the homozygous mice therefore died during the perinatal period.

TABLE 1

Genotypes of mice generated from heterozygous breeding.

| Genotype | -/- | +/- | +/+ |
|---|---|---|---|
| Prenatal mice | | | |
| E 10.5 | 3 | 7 | 3 |
| E 12.5 | 6 | 3 | 5 |
| E 13.5 | 5 | 15 | 10 |
| E 15.5 | 6 | 13 | 9 |
| E 16.5 | 9 | 19 | 7 |
| Postnatal mice | | | |
| P 5-P 20 | 11 | 246 | 160 |

Prenatally, Caspase-9 -/- fetuses exhibited highly repeatable CNS abnormalities such as hypercellularity and ventricular hypertrophy similar to observations in the Caspase-3 knockout mice [K. Kuida et al., Nature, 384, pp. 368-72 (1996)]. Interestingly, homozygous mice did not show any gross abnormalities in other organs. The rare homozygous mice which survived birth possessed only subtle differences, if any, in the brain. We believe that the genetic background of individual mice influenced this variability in the phenotype of postnatal Caspase-9 -/- as has been shown in p53 deficient mice [V. P. Sah et al., Nat. Genetics, 10, pp. 175-80 (1995)].

EXAMPLE 2

RT-PCR Analysis of caspase-9 mRNA

Total RNA was isolated from the kidney of the Caspase-9 knockout mice by Trizol reagent (Gibco-BRL). Five micrograms of total RNA was reverse-transcribed using the superscript pre-amplification system (Gibco-BRL) and the resulting templates were subjected to a PCR reaction with caspase-9 specific primers (5'-GCC ATG GAC GAA GCG GAT CGG CGG-3' (SEQ ID NO:3) and 5'-GGC CTG GAT GAA GAA GAG CTT GGG (SEQ ID NO:4)) or primers specific for (-actin [Chang et al., J. Exp. Med., 180, pp. 1367-74 (1994)].

The absence of intact caspase-9 mRNA in Caspase-9 -/- mice was confirmed by RT-PCR analysis (FIG. 1B).

EXAMPLE 3

Northern Blot Analysis

In order to examine mRNA expression of genes implicated in the caspase cascade, Northern blot analysis was performed throughout development of wild-type mice with specific probes for caspase-9, caspase-3 and apaf-1.

Poly(A)+RNA blots (Clontech) were hybridized overnight with random primed human caspase-9 cDNA, hamster caspase-3 cDNA [Wang et al., EMBO J., 15, pp. 1012-20 (1996)], or human apaf-1 cDNA in Express-hyb buffer (Clontech) at 37° C. The apaf-1 cDNA was amplified from HeLa Marathon-Ready cDNA (Clontech) by PCR using apaf-1-specific primers (5'-GGG AAG ATG GAT GCA AAA GCT CGA-3' (SEQ ID NO:5) and 5'-CTG GCT GCA ATT CTT CTC TGT AAG-3' (SEQ ID NO:6)). The blots were washed with 2×SSC/0.1% SDS for 1 hr at room temperature followed by 0.2×SSC/0.1% SDS for 1 hr at 50° C. The blots were then analyzed with a Fuji BAS-1500 bio-image analyzer.

As shown in FIG. 1C, caspase-9 mRNA is expressed as early as E7 and is then down-regulated after E15. In contrast, both caspase-3 and apaf-1 mRNA are up-regulated beginning at E11 and are stably expressed thereafter. Thus, all three genes are expressed together and are likely to form a functional apoptotic pathway after E7.

EXAMPLE 4

Histology and Immunocytochemistry

Fetuses fixed in 4% paraformaldehyde were embedded in paraffin and cut in 10 μm increments. Coronal brain or horizontal body sections were stained with 0.1% cresyl violet. For semi-thin sections, embryos were fixed in 4% paraformaldehyde and 1.5% glutaraldehyde, embedded in plastic, and serial 1 μm sections were stained with 1% toluidine blue.

Figure 2A:
FIG. 2 depicts the neuronal phenotype in Caspase-9 +/− and Caspase-9 −/− mouse embryos at E10.5 (panels A and B), E13.5 (panels C and D) and E16.5 (panels E and F).
Figure 2B:
Figure 2C:
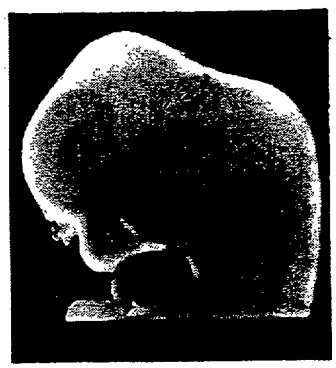
Figure 2D:
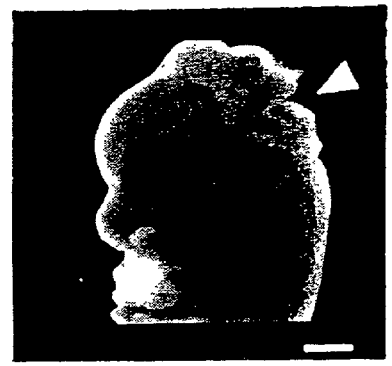
Figure 2E:
Figure 2F:

The neuronal phenotype of Caspase-9 -/- mice is apparent externally as soon as E10.5 (FIG. 2A and 2B) as a defect in closure of the dorsal neural tube at the junction between the midbrain and the hindbrain. At E13.5 (FIG. 2C and 2D), this dorsal defect is still evident although no defects are outwardly apparent in other CNS structures (e.g. telencephalon and spinal cord). However, by E16.5 (FIG. 2E and 2F) there is prominent exencephaly with the entire brain above the level of the hindbrain exposed outside of the head. In addition, the protruding brain appears larger and altered in morphology. It is presumably these alterations which shift the position of the brain with respect to landmarks in the head.

Figure 3A:
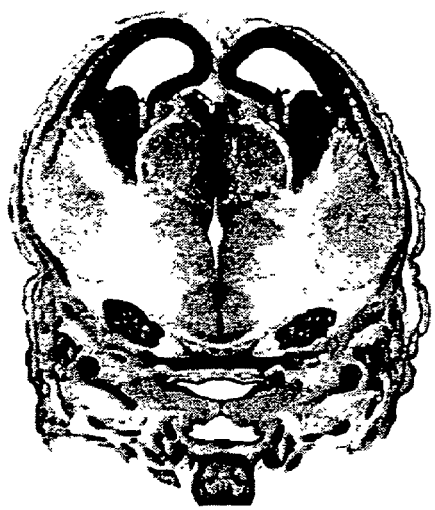
FIG. 3 depicts Nissl-stained brain sections from Caspase-9 +/− and Caspase-9 −/− mouse embryos at E13.5 (panels A and B), a higher magnification of the same sections (panels C and D); Nissl-stained brain sections from Caspase-9 +/− and Caspase-9 −/− mouse embryos at E16.5 (panels E and F) and spinal cord sections from Caspase-9 +/− and Caspase-9 −/− mouse embryos at E16.5 (panels G and H).
Figure 3B:
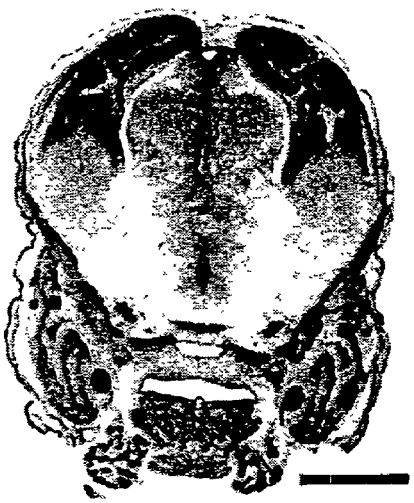
Figure 3C:
Figure 3D:
Figure 3E:
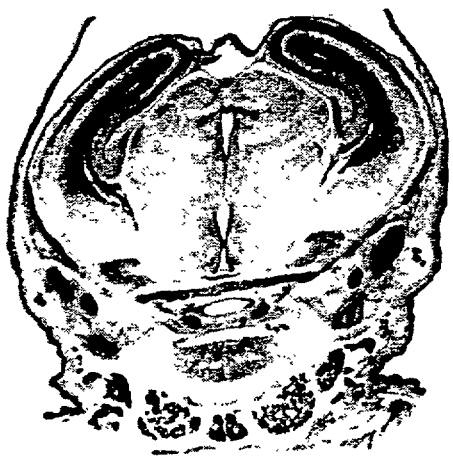
Figure 3F:
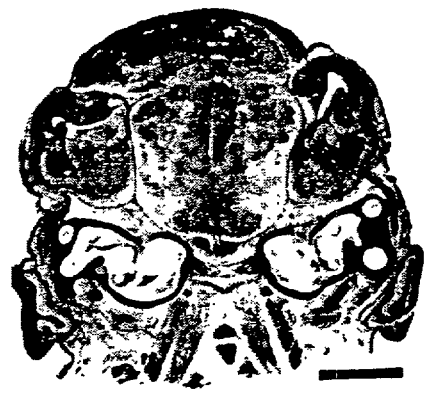
Figure 3G:
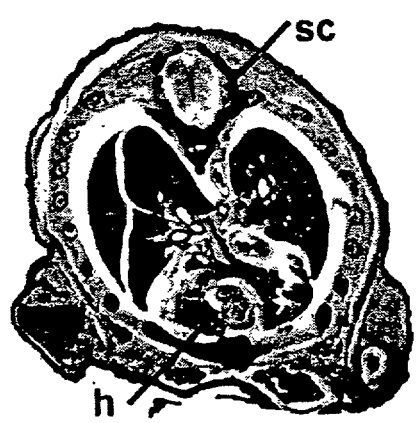
Figure 3H:
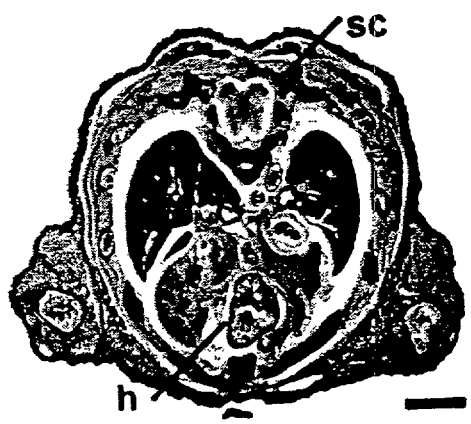

Examination of the Caspase-9 -/- histological sections reveals widespread enlargement of the proliferative populations in the forebrain and midbrain as well as stenosis of the cerebral ventricles. At E13.5 (FIG. 3A and 3B), the thalamus is larger and the lateral and third ventricles are obstructed. In addition, there are discontinuities and heterotopias evident in the telencephalic wall with the proliferative ventricular zone and postmitotic cortical plate completely interrupted and invaginated (FIG. 3C and 3D). By E16.5, the appearance of the brain is markedly altered with displacement of the telencephalic vesicles by an expanded midbrain population which protrudes on top of the brain (FIG. 3E and 3F). The dark staining in Caspase-9 -/- brain sections indicates that more proliferative cells are present compared to controls. In contrast, the size and development of the spinal cord appears unaffected in Caspase-9 -/- mice as are other non-neural organs such as the heart and lungs (FIG. 3G and 3H).

Figure 4A:
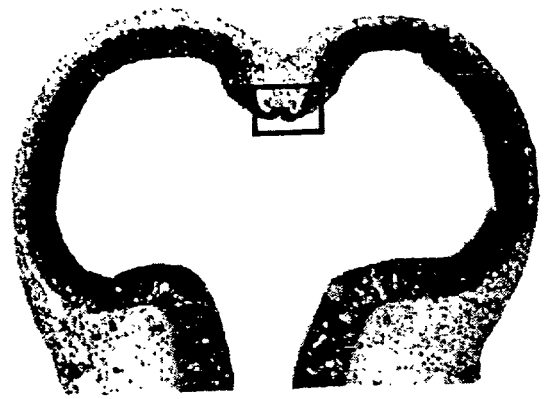
FIG. 4 depicts semi-thin Nissl-stained horizontal sections of the forebrain of Caspase-9 +/− and Caspase-9 −/− mouse embryos at E10.5 (panels A and B). A higher magnification of the boxed areas in panels A and B is shown in panels C and D. Panel E depicts TUNEL staining of a horizontal brain section of a Caspase-9 −/− mouse embryo at E12. Panel F depicts the distribution of TUNEL$^+$ cells in Caspase-9 +/+ and Caspase 9 −/− embryos.
Figure 4B:
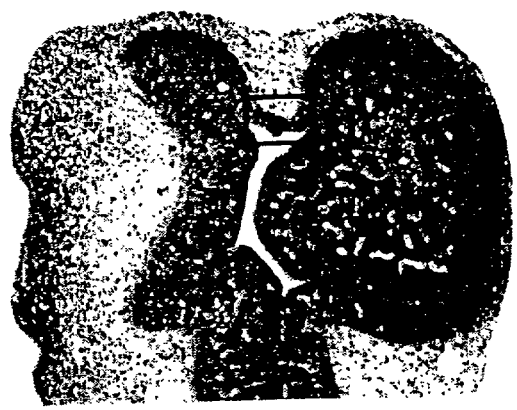
Figure 4C:
Figure 4D:

To determine the mechanism underlying the gross structural changes in the Caspase-9 -/- forebrain, we examined the effect of the knockout on the incidence of cells dying by apoptosis. In horizontal semi-thin sections at E10.5 (FIG. 4A and 4B), the enlarged telencephalic epithelium obscures the ventricle in the mutants. Moreover, pyknotic cells usually observed during normal brain development were absent in Caspase-9 -/- embryos. For example, pyknotic clusters in the lamina terminalis of the forebrain, representing the morphogenetic cell death which eventually separates the hemispheres (FIG. 4C and 4D), are eliminated with the resulting lamina thicker due to increases in the number of cells and cell density.

EXAMPLE 5

TUNEL Staining

For TUNEL stains to detect DNA fragmentation, 4% paraformaldehyde-fixed E12 heads were cryoprotected in 30% sucrose, frozen, and sectioned horizontally. Frozen 20 μm horizontal brain sections were incubated in 0.26 U/ml TdT and 1× of supplied buffer (Life Technologies), and 20 μM biotinylated-16-dUTP (Boeringher Mannheim) for 60 min. at 37° C. Sections were then washed three times in PBS (pH 7.4) and blocked for 30 min. with 2% BSA in PBS (pH 7.4). The sections were then incubated with FITC-coupled streptavidin (Jackson Immunoresearch) 1:100 in PBS for 30 minutes, rinsed, and then counterstained with the nuclear stain propidium iodide (1 μg/ml, Sigma).

Figure 4E:
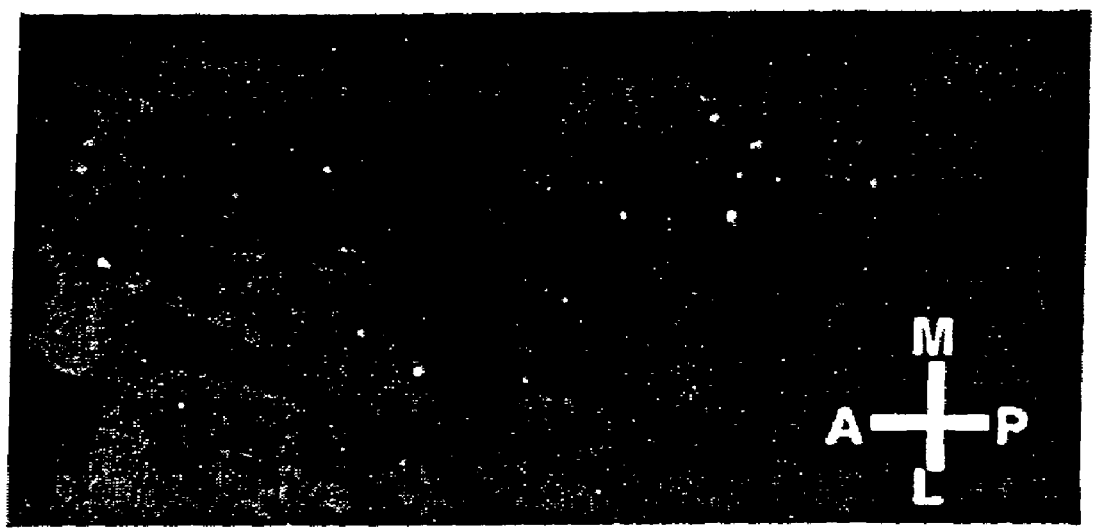
Figure 4F:
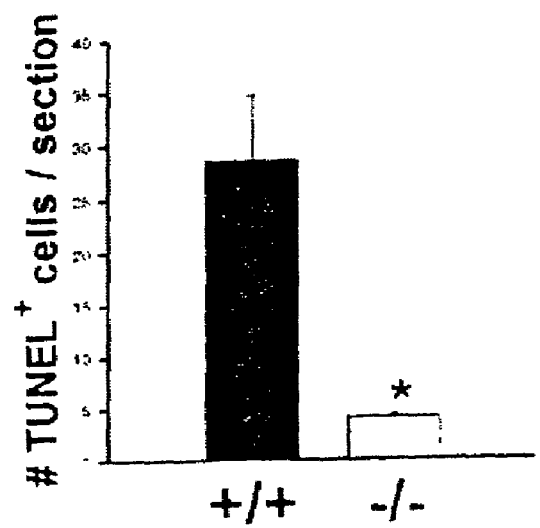

The result of TUNEL assays on E12 brain sections is shown in FIG. 4E. We measured a nearly ten-fold reduction in the number of TUNEL-positive cells throughout the brain in the Caspase-9 knockouts (FIG. 4F). These data clearly indicate that the brain malformations in Caspase-9 −/− mice are due to reduced apoptosis and that Caspase-9 mediated apoptosis is therefore crucial for normal brain development in vivo.

EXAMPLE 6

Apoptosis Assay Using Thymocytes

To investigate the role of Caspase-9 in apoptosis pathways in other systems, we used primary cultures of thymocytes. Although thymocytes from Caspase9 −/− animals developed normally with no differences in the number of thymocytes or in the ratio of surface markers such as CD4, CD8 or CD3 (data not shown), we challenged the thymocytes with several apoptotic stimuli: dexamethasone, staurosporine, and anti-Fas antibody Thymocytes were isolated from wild type and Caspase9 −/− mice. One million cells were treated with 2 μM dexamethasone (Sigma), 1 μM staurosporine (Sigma), 1 μg/ml anti-mouse Fas antibody (PharMingen) plus 30 mg/ml cycloheximide (Sigma), or 10% FCS medium only for 6 hr or 24 hr. Samples were stained with Annexin V (Boehringer Mannheim) and 7-aminoactinomycin D (7-AAD) (Sigma) to label apoptotic cells for FACS Sort (Becton Dickinson).

Although no differences in the kinetics of thymocyte survival were previously observed between wild type and Caspase-3−/− mice [K. Kuida et al., Nature, 384, pp. 368-72 (1996)], Caspase-9 −/− thymocytes did exhibit variable responses to these apoptosis-inducing stimuli. Caspase-9 deficient thymocytes were resistant to dexamethasone-induced cell death. Caspase-9 −/− staurosporine-induced thymocytes exhibited reduced survival which was comparable to the death seen in controls (data not shown). In addition, knock-out thymocytes did undergo apoptosis in response to anti-Fas antibody application in a manner similar to wild type cells.

EXAMPLE 7

DNA Fragmentation Assay

DNA was isolated using a DNA isolation kit (LeMax Biotech) and subjected to electrophoresis on a 2% agarose gel. Gels were stained by ethidium bromide and images were taken by a scanner.

Caspase-9 deficient thymocytes did not undergo DNA laddering even after 24 hours of treatment with dexamethasone. DNA laddering was also eliminated in response to staurosporine. In addition, knockout thymocytes did undergo DNA laddering.

These data suggest that while Caspase-9 may be necessary for dexamethasone-induced cell death, other mechanisms mediate staurosporine and Fas death pathways. Different insults therefore appear to employ separate apoptotic pathways even in the same cell type. Interestingly, however, Caspase-9 −/− thymocytes did begin to cleave their DNA after 36 and 48 hours of continual dexamethasone and staurosporine treatment (data not shown), indicating that long-term insults can eventually bypass the block on DNA laddering imposed by Caspase-9 deletion.

EXAMPLE 8

Assay for Cleavage of Caspase-3

To investigate the functional consequences of Caspase-9 deletion, we used an in vitro method to assay the activation of downstream caspases such as Caspase-3.

Full-length human caspase-3 cDNA was transcribed and translated using TNT quick coupled transcription/translation system (Promega) and $^{35}S$ methionine (Amersham). To generate the recombinant Caspase-9, full length caspase-9 cDNA was translated using the same system. S-100 cytosolic fractions were obtained as described by Liu et al., Cell, 86, pp. 147-57 (1996). An aliquot of in vitro-translated Caspase-3 was incubated with 20 μg of S-100 cytosolic fraction in the presence of 1 mM of additional $MgCl_2$ with or without cytochrome c or DATP at 30° C. for 1 hr in a final volume of 20 μl. For reconstitution of Caspase-9 activity, 5 μl of the translated reaction or reticulocyte lysate was added to the reaction. At the end of incubation, 7 μl of 4×SDS sample buffer was added to each reaction and samples electrophoresed on a 16% SDS-PAGE gel. Gels were dried and exposed to a phosphoimaging plate and analyzed by Fuji BAS-1500 bio-image analyzer.

Figure 5A:
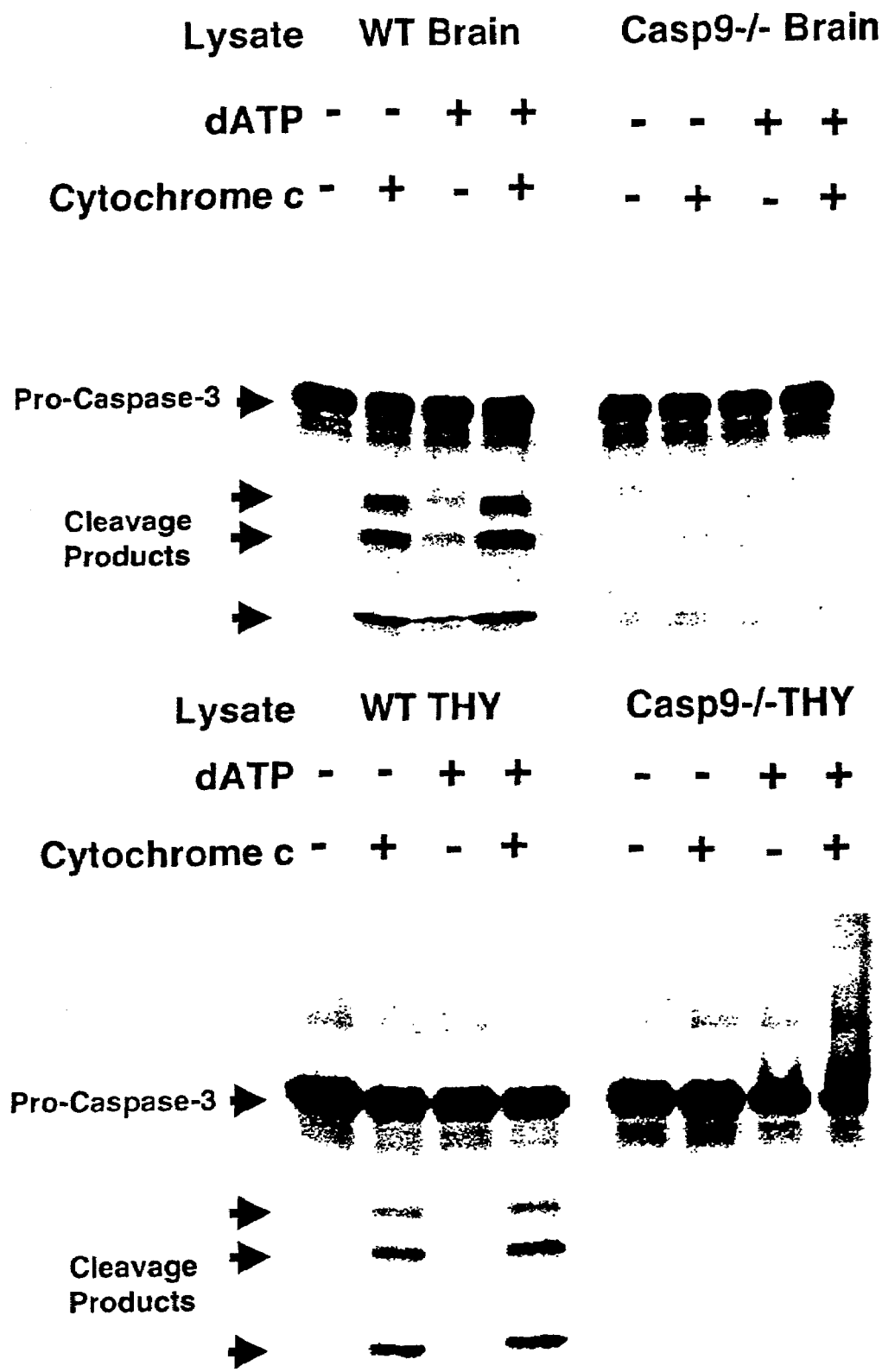
FIG. 5, panel A, depicts an SDS-polyacrylamide gel electrophoresis of $^{35}$S-methionine labeled caspase-3 treated with an S-100 cytosolic fraction from Caspase-9 −/− E15.5 and Caspase-9 −/− embryonic brains or thymocytes in the presence or absence of dATP andlor cytoebrome c. Panel B depicts an SDS-polyacrylamide gel electrophoresis of $^{35}$S-methionine labeled caspase-3 treated with an S-100 cytosolic fraction from Caspase-9 −/− E15.5 embryonic brains in the presence or absence of dATP, eytochrome c and/or in vitro transcribed and translated Caspase-9.
Figure 5B:
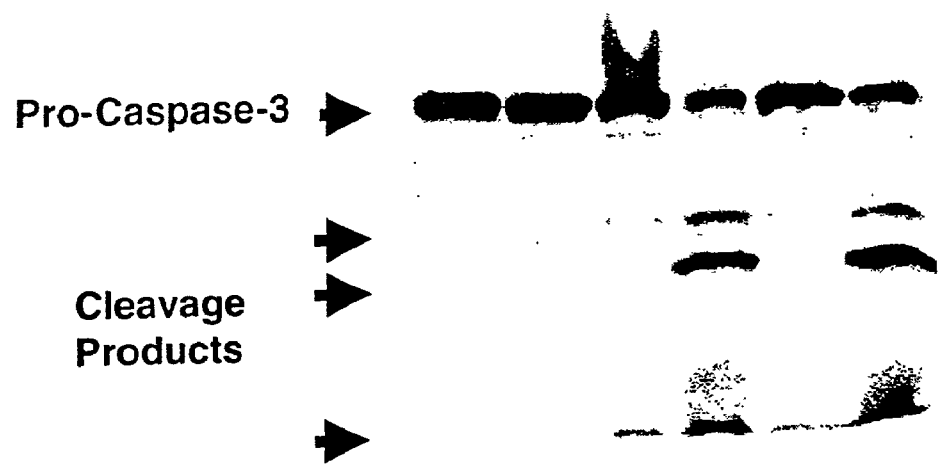

While wild type S-100 cytosolic fractions could cleave Caspase-3, cytosolic fractions isolated from Caspase-9 −/− cells could not cleave Caspase-3 (FIG. 5, panel A). These data demonstrate that Caspase-9 is a necessary caspase upstream in the activation pathway and that the phenotypes we observed in Caspase-9 −/− animals are due to the lack of activation of downstream caspases such as Caspase-3.

Moreover, the addition of in vitro translated Caspase-9 to S-100 cytosolic extracts from Caspase-9 −/− brain cells reconstituted the ability to cleave Caspase-3, suggesting that all other required elements are present in Caspase-9 −/− cells (FIG. 5. panel B).

Interestingly, and in contrast to a previous report [Liu et al., Cell, 86, pp. 147-57 (1996)], lysates from control cells which could cleave the downstream caspase did not require additional dATP (FIG. 5 panels A and B). This suggests that the intracellular concentration of dATP in the tissues we used was high enough to activate Apaf-1 and that the release of cytochrome c is the required element for initiation of the activation process.

The absence of in vitro Caspase-3 cleavage in the Caspase-9 −/− brain lysates suggested that the brain malformations in the mutants may be caused by a compromised Caspase-3 dependent apoptotic pathway in vivo. To test this possibility, we examined the in vivo activation of Caspase-3 using an antibody (CM1) specific for the p20 subunit of Caspase-3 which only recognizes activated Caspase-3.

E12.5 day embryos were fixed in Bouin's solution, cryoprotected in 30% sucrose and then sectioned horizontally.

Figure 6A:
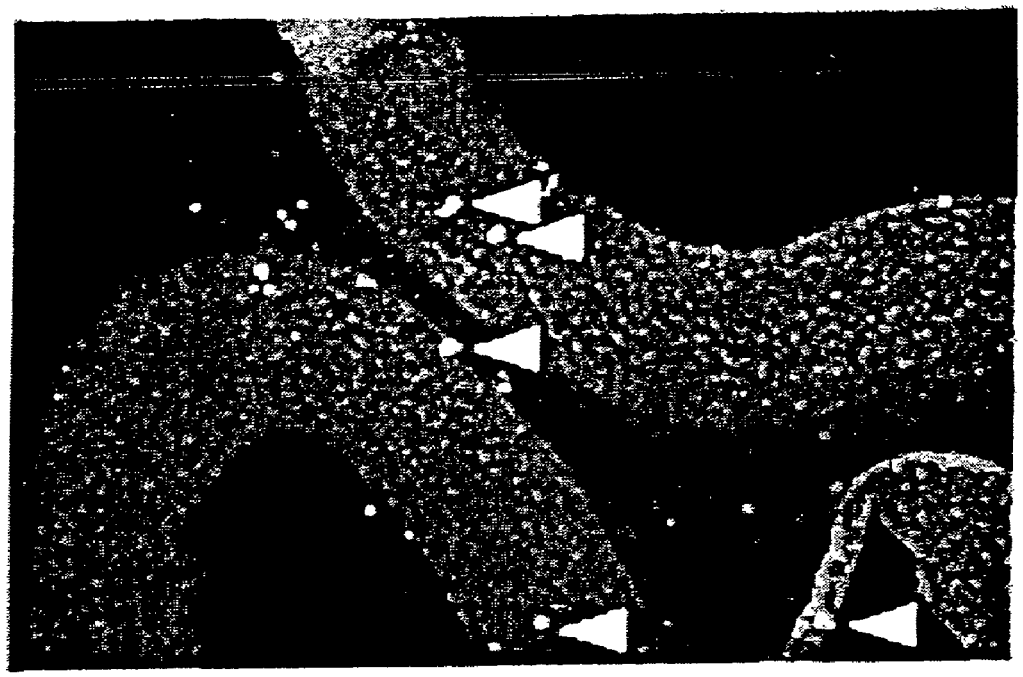
FIG. 6 depicts brain sections from Caspase-9 +/+ (panel A) or −/− (panel B) E12.5 embryos stained with an antibody specific for activated Caspase-3.
Figure 6B:
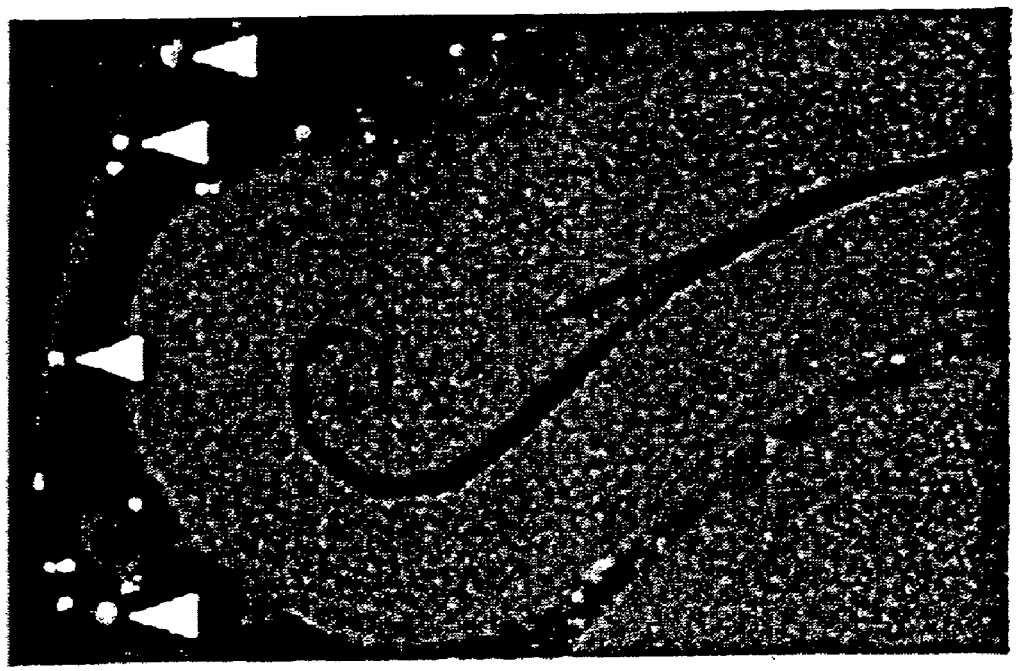

In E12.5 wild type and heterozygous embryos, positive staining for activated Caspase-3 was found in the ectodermal surface and sporadically distributed throughout the developing nervous system (FIG. 6. panel A). Under high magnification, staining for active Caspase-3 was present both in the cytoplasm and in the condensed nucleus (data not shown). In contrast, although CM1-positive cells were seen in the meningeal and ectodermal surfaces of Caspase-9 −/− embryos, no such staining was found within the nervous tissue (FIG. 6. panel B). Therefore, these results indicate that Caspase-9 is upstream and critical to the activation of Caspase-3 in the developing nervous system in vivo.

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

We claim:

1. A genetically altered mouse comprising a defective genomic Caspase-9 gene, said defective genomic Caspase-9 gene resulting in a deficiency in functional Caspase-9 expression in the mouse, and said defective genomic Caspase-9 gene, when homozygous, resulting in reduced apoptosis in brain, spinal cord, dexamethasone-treated thymocytes, cardiac muscle, or smooth muscle, or reduced apoptosis associated with viral infection.

2. The genetically altered mouse according to claim 1, wherein said mouse is heterozygous for the defective genomic Caspase-9 gene.

3. The genetically altered mouse according to claim 1, wherein said mouse is homozygous for the defective genomic Caspase-9 gene.

4. A genetically altered mouse comprising a defective genomic Caspase-9 gene, said defective genomic Caspase-9 gene comprising a DNA sequence encoding a Caspase-9 protein that does not contain the pentapeptide motif QACXG (SEQ ID NO: 7) and resulting in a deficiency in functional Caspase-9 expression in the mouse, and said defective genomic Caspase-9 gene, when homozygous, resulting in reduced apoptosis in brain, spinal cord, dexamethasone-treated thymocytes, cardiac muscle, or smooth muscle, or reduced apoptosis associated with viral infection.

5. The genetically altered mouse according to claim 4, wherein said mouse is heterozygous for the defective genomic Caspase-9 gene.

6. The genetically altered mouse according to claim 4, wherein said mouse is homozygous for the defective genomic Caspase-9 gene.

7. A method of producing a genetically altered mouse comprising a defective genomic Caspase-9 gene, said defective genomic Caspase-9 gene resulting in a deficiency in functional Caspase-9 expression in the mouse, and said defective genomic Caspase-9 gene, when homozygous, resulting in reduced apoptosis in brain, spinal cord, dexamethasone-treated thymocytes, cardiac muscle, or smooth muscle, or reduced apoptosis associated with viral infection, the method comprising the steps of:

a. providing an isolated DNA sequence comprising a genomic DNA sequence encoding a mouse Caspase-9 that is defective in that it does not contain the pentapeptide motif QACXG (SEQ ID NO: 7), wherein "X" is arginine or glycine;

b. introducing said isolated DNA sequence into a mouse embryonic stem cell under conditions that cause the genomic DNA sequence to stably integrate, via homologous recombination, into a chromosome of said stem cell;

c. Incorporating said stem cell into a mouse blastocyst to produce a chimeric mouse;

d. breeding said chimeric mouse to produce mice heterozygous for said genomic DNA sequence encoding said defective genomic Caspase-9 gene, thereby producing the genetically altered mouse.

8. The method according to claim 7, wherein said isolated DNA sequence additionally comprises a selectable marker gene.

9. The method according to claim 8, wherein said marker gene is a neo gene.

10. The method of claim 7, further comprising:

e. interbreeding said mice heterozygous for the genomic DNA sequence encoding the defective genomic Caspase-9 gene to produce homozygous mice deficient in functional Caspase-9 expression.

* * * * *